(12) United States Patent
Shi et al.

(10) Patent No.: US 8,632,481 B2
(45) Date of Patent: Jan. 21, 2014

(54) THERAPEUTIC SHOE

(75) Inventors: Zheng Shi, Shenzhen (CN); Jiang-Feng Liu, Shenzhen (CN)

(73) Assignees: Shenzhen Futaihong Precision Industry Co., Ltd., Shenzhen (CN); FIH (Hong Kong) Limited, Kowloon (HK)

( * ) Notice: Subject to any disclaimer, the term of this patent is extended or adjusted under 35 U.S.C. 154(b) by 314 days.

(21) Appl. No.: 13/101,274

(22) Filed: May 5, 2011

(65) Prior Publication Data

US 2012/0260531 A1      Oct. 18, 2012

(30) Foreign Application Priority Data

Apr. 18, 2011   (CN) .......................... 2011 1 0096199

(51) Int. Cl.
  *A61H 1/00*      (2006.01)
(52) U.S. Cl.
  USPC ........................................................... 601/78
(58) Field of Classification Search
  USPC ........... 601/46, 27–31, 56–60, 62, 66, 78–81; 36/141
  See application file for complete search history.

(56) References Cited

U.S. PATENT DOCUMENTS

| | | | |
|---|---|---|---|
| 1,272,931 A * | 7/1918 | Etheridge | 36/2.6 |
| RE19,817 E * | 1/1936 | Wurzbach et al. | 310/29 |
| 3,848,588 A * | 11/1974 | Miquel | 601/78 |
| 5,235,761 A * | 8/1993 | Chang | 36/3 R |
| 5,483,759 A * | 1/1996 | Silverman | 36/137 |
| 5,592,759 A * | 1/1997 | Cox | 36/141 |
| 6,258,048 B1 * | 7/2001 | Montague | 601/19 |
| 7,487,606 B2 * | 2/2009 | Koo et al. | 36/141 |
| 7,614,168 B1 * | 11/2009 | Zummer et al. | 36/141 |
| 8,398,570 B2 * | 3/2013 | Mortimer et al. | 601/46 |
| 2008/0015477 A1 * | 1/2008 | Talish et al. | 601/79 |
| 2011/0271554 A1 * | 11/2011 | Jazdanian | 36/43 |
| 2013/0072835 A1 * | 3/2013 | Harry et al. | 601/46 |

FOREIGN PATENT DOCUMENTS

WO    WO2010/079207    *  7/2010

* cited by examiner

*Primary Examiner* — Kristen Matter

(74) *Attorney, Agent, or Firm* — Altis Law Group, Inc.

(57) ABSTRACT

A therapeutic shoe includes a main body, a sole located at one side of the main body, a vibration layer, and a power generating module. The vibration layer is located between the main body and the sole. The power generating module includes a power generating unit, a rectifying circuit and a vibration device, which are electrically connected in series. The power generating unit generates and induces induced current. The rectifying circuit receives, rectifies, amplifies and processes the induced current from the power generating unit. The vibration device is located at the vibration layer and receives the processed induced current from the rectifying circuit to vibrate according to a predetermined vibration frequency in the vibration layer.

20 Claims, 2 Drawing Sheets

THERAPEUTIC SHOE

CROSS-REFERENCE TO RELATED APPLICATION

This application is related to a co-pending U.S. patent application Ser. No. 13/101,272, entitled "HEATED SHOE", by Zhen Shi et al. Said application has the same assignee as the present application and is concurrently filed herewith. The disclosure of the above-identified application is incorporated herein by reference.

BACKGROUND

1. Technical Field

The disclosure generally relates to shoes, and more particularly to a therapeutic shoe with massage function.

2. Description of the Related Art

Different therapeutic insoles mixed with therapeutic protective remedies are typically used in shoes to achieve therapeutic purposes. However, the therapeutic insoles cannot always physically massage and stimulate therapeutic points of the feet (such as acupuncture or acupressure points), so the therapeutic effects of the therapeutic shoes are not always very satisfactory. Moreover, after a period of use, therapeutic performance of the therapeutic insoles gradually weakens due to volatilization of the therapeutic protective remedy. Thus, the users need to constantly replace the old insoles to maintain the therapeutic effects, resulting in increased cost.

Therefore, there is room for improvement within the art.

BRIEF DESCRIPTION OF THE DRAWINGS

Many aspects of an exemplary therapeutic shoe can be better understood with reference to the following drawings. The components in the drawings are not necessarily drawn to scale, the emphasis instead being placed upon clearly illustrating the principles of the exemplary therapeutic shoe. Moreover, in the drawings, like reference numerals designate corresponding parts throughout the several views. Wherever possible, the same reference numbers are used throughout the drawings to refer to the same or like elements of an embodiment.

DETAILED DESCRIPTION

Figure 1:
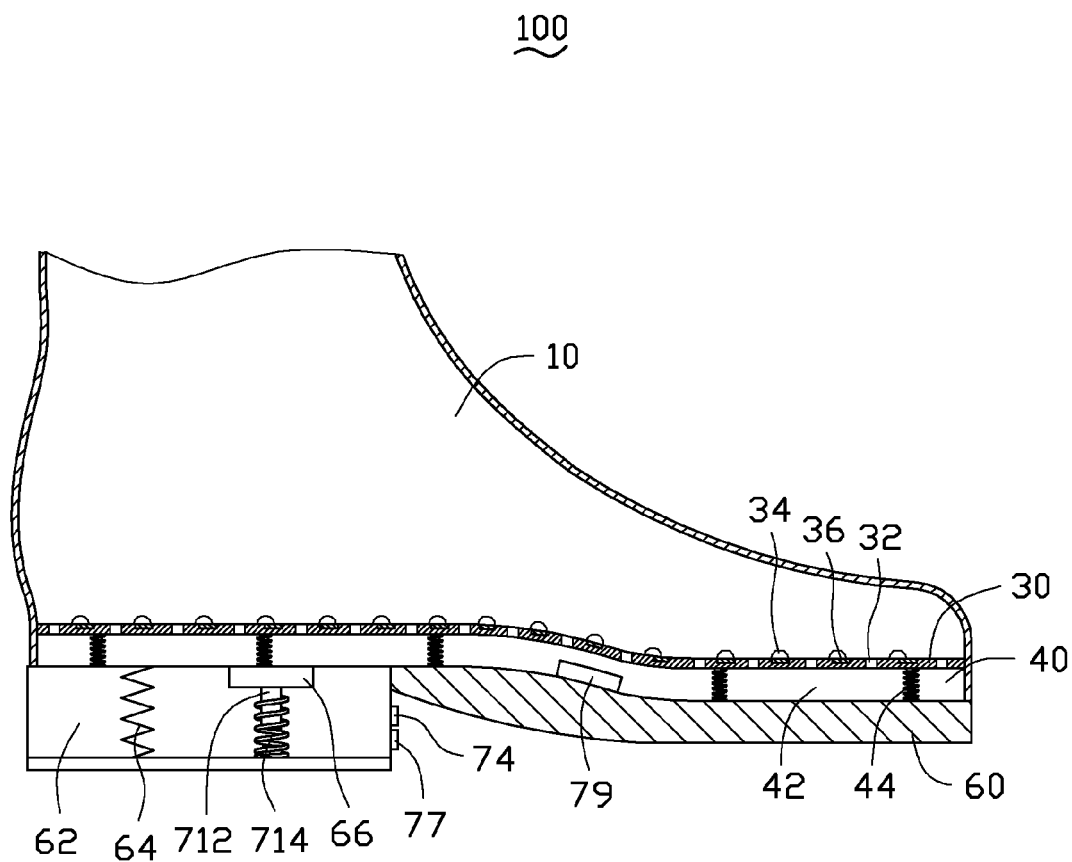
FIG. 1 is a cut-away view of a therapeutic shoe, according to an exemplary embodiment of the disclosure.

FIG. 1 shows a therapeutic shoe 100, according to an exemplary embodiment of the disclosure. The therapeutic shoe 100 can automatically generate electric energy through electromagnetic induction and physically massage, and stimulate therapeutic points (such as acupuncture or acupressure points) of feet of users to achieve therapeutic effects.

Figure 2:
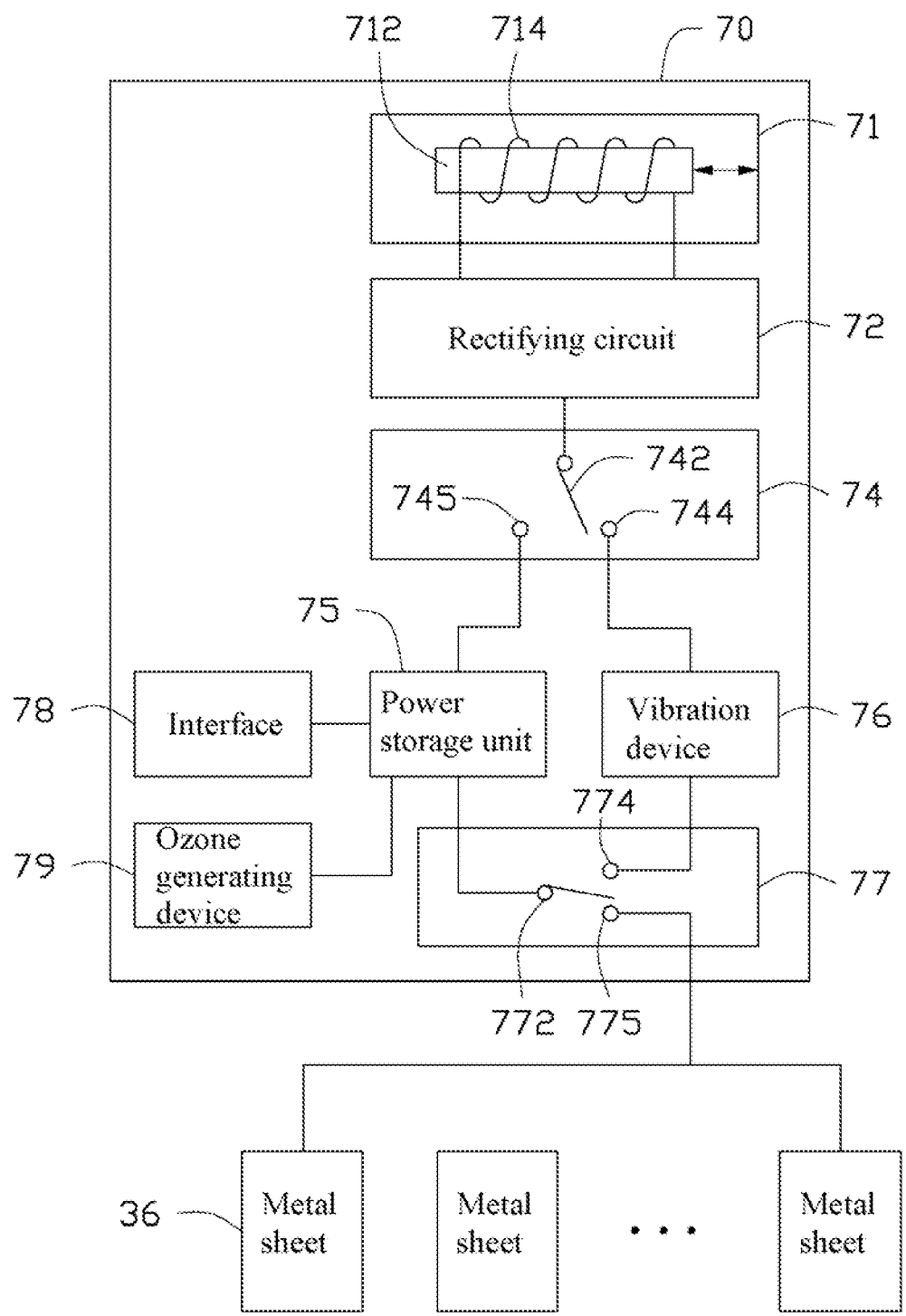
FIG. 2 is a block view of a power generating module and a plurality of metal sheets of the therapeutic shoe as shown in FIG. 1 of the disclosure.

Also referring to FIG. 2, the therapeutic shoe 100 includes a main body 10, an insole 30, a vibration layer 40, a sole 60, and power generating module 70. The insole 30 and the vibration layer 40 are located between the main body 10 and the sole 60 in turn.

The insole 30 is located within the main body 10 and can be made from soft magnetic material or be an insole with soft material layer, having magnetotherapy and therapeutic benefits. The insole 30 defines a plurality of through holes 32, the through holes 32 are evenly distributed on the surface of the insole 30 and are capable of ventilation and heat output, and are conducive to maintaining dryness of the therapeutic shoe 100.

The insole 30 further includes a plurality of massage projections 34 and a plurality of metal sheets 36. The massage projections 34 are distributed and arranged on the surface of the insole 30 corresponding to the therapeutic points of the feet. Thus, the massage projections 34 can massage and stimulate the therapeutic points through physical vibration, which can help eliminate fatigue and play a role in therapeutic care. The metal sheets 36 are distributed and located on the insole 30 adjacent to the massage projections 34, substantially corresponding to and aligned with the therapeutic points.

The vibration layer 40 is located adjacent to the upper side of the insole 30 and includes an accommodating space 42 and a plurality of elastic pieces 44. In this exemplary embodiment, the accommodating space 42 can be a hollow cavity. The elastic pieces 44 can be springs, and are received and are evenly arranged within the accommodating space 42.

The sole 60 is located at one side of the main body 10 and can be made of elastic material, therefore, the sole 60 is capable of elastically deforming and automatically restoring its initial shape after elastic deformation. The sole 60 defines a receiving space 62 substantially at the heel of the therapeutic shoe 100. The receiving space 62 is capable of partially receiving the power generating module 70.

The power generating module 70 is capable of generating induced current by electromagnetic induction and includes a power generating unit 71, a rectifying circuit 72, a first switch 74, a power storage unit 75, a vibration device 76, and a second switch 77. The power generating unit 71 includes a magnet 712 and a coil 714.

In this exemplary embodiment, the magnet 712 can be a substantially cylindrical or rectangular shaped permanent magnet and is located at the upper wall of the receiving space 62. The coil 714 can be made of copper, and is a substantially cylindrical or rectangular shaped inductive coil corresponding to the shape of the magnet 712. The coil 714 is located at the bottom wall of the receiving space 62 and is aligned with the magnet 712. Thus, when the sole 60 is elastically deformed or is restored from elastic deformation, the sole 60 drives the magnet 712 to reciprocate in the coil 714. Thus, the coil 714 cuts magnetic field lines of the magnet 712 to generate induced current according to the principle of electromagnetic induction.

The rectifying circuit 72 is in electronic communication with the coil 714 of the power generating unit 71, and substantially includes transformers, rectifiers, filters, rectifier diodes, and other electronic components. The rectifying circuit 72 is capable of receiving, rectifying, amplifying, and converting the induced current, which periodically reversers direction, from the coil 714 into corresponding direct current (DC).

The first switch 74 can be a single pole double throw (SPTT) switch, and includes a common end 742, a first fixed contact 744 and a second fixed contact 745. The common end 742 is in electronic communication with the rectifying circuit 72, and the first fixed contact 744 and the second fixed contact 745 are electrically connected to the vibration device 76 and the power storage unit 75, respectively.

The power storage unit 75 can be a storage battery and is capable of storing electric energy from the rectifying circuit 72 and providing the electric energy for the vibration device 76. In this exemplary embodiment, when the common end 742 of the first switch 74 is switched on to electrically connect the second fixed contact 745, the power storage unit 75 electrically connects the rectifying circuit 72, and receives and stores the electric energy from the rectifying circuit 73.

The vibration device 76 can be a vibrator or a vibrating motor and is located at the upper wall of the accommodating space 42 of the vibration layer 40. In this exemplary embodiment, when the common end 742 of the first switch 74 is switched on to electrically connect the first fixed contact 744 of the first switch 74, the rectifying circuit 72 is electrically connected to and powers the vibration device 76, the vibration device 76 is activated and vibrates according to a predetermined vibration frequency, enabling the massage projections 34 to continually stimulate and physically massage the therapeutic points of the feet.

The second switch 77 can be a SPDT switch and includes a first common end 772, a first fixed contact 774 and a second fixed contact 775. In this exemplary embodiment, the common end 772 is in electronic communication with the power storage unit 75, and the first fixed contact 774 and the second fixed contact 775 are in electronic communication with vibration device 76 and the metal sheets 36, respectively. In detail, when the common end 772 of the second switch 77 is switched on to electrically connect the first fixed contact 774 of the second switch 77, the power storage unit 75 selectively connects and powers the vibration device 76, and the vibration device 76 is activated and vibrates according to a predetermined vibration frequency to stimulate and massage the therapeutic points. When the common end 772 of the second switch 77 is switched on to electrically connect the second fixed contact 775 of the second switch 77, the power storage unit 75 selectively and electrically connects the metal sheets 36, so the current from the power storage unit 75 flows to the feet to stimulate the therapeutic points, which substantially achieves the effects of massage.

Also referring to FIGS. 1 and 2, in use, the users press and step on the sole 60 in the course of walking or exercise, enabling the sole 60 to elastically deform and restore, so the magnet 712 moves back and forth alternately in the coil 714. Thus, the closed coil 714 continues to cut the magnetic field lines of the magnet 712 to induce and generate induced current within the coil 714. The rectifying circuit 72 rectifies, amplifies and processes the induced current from the coil 714, and converts the processed induced current into corresponding stable DC. When the common end 742 of the first switch 74 is switched on to electrically connect the fixed contact 744 of the first switch 74, the rectifying circuit 72 electrically connects and powers the vibration device 76, so the vibration device 76 is activated and vibrates according to a predetermined vibration frequency, driving the massage projections 34 of the insole 30 to continually stimulate and massage the therapeutic points of the feet. When the common end 742 of the first switch 74 is switched on to electrically connect the second fixed contact 745 of the first switch 74, the power storage unit 75 electrically connects the rectifying circuit 72, and receives and stores the electric energy from the rectifying circuit 72.

In this exemplary embodiment, when the users are not moving, the common end 772 of the second switch 77 is switched to the first fixed contact 774 of the second switch 77, the power storage unit 76 then electrically connects the vibration device 76 through the second switch 77, so the vibration device 76 is activated and starts to vibrate according to a predetermined vibration frequency and drives the massage projections 34 to continually stimulate and massage the therapeutic points.

The power generating module 70 further includes an interface 78, which includes hardware and associated circuitry and is implemented to link one device with another. In this exemplary embodiment, the interface 78 is electrically connected to the power storage unit 75, so the power storage unit 75 can electrically connect to an electronic device (not shown), such as a mobile phone, to power the electronic device.

Moreover, the sole 60 further includes at least one spring 64 received within the receiving space 62. The opposite ends of each spring 64 are fixed at the upper wall and the bottom wall of the receiving space 62 respectively. Thus, the springs 64 and the sole 60 elastically deform and restore elastic deformation to force the magnet 712 to reciprocate in the coil 714, so the closed coil 714 cuts the magnetic field lines of the magnet 712 to generate induced current.

Additionally, the sole 60 further includes an iron plate 66. The iron plate 66 is located on and adjacent to the magnet 712, and is capable of maintaining and enhancing the magnetism of the magnet 712.

The insole 30 can further include infrared material, which can play a role in infrared physical therapy. The power generating module 70 further includes an air treatment device located at the accommodating space 42 of the vibration layer 40. The air treatment device can disinfect, sterilize, or deodorize the air in the therapeutic shoe 100. The air treatment device may includes an ozone generating device 79 electrically connected to the power storage unit 75.

In addition, the power generating module 70 can also be a hand pressing type of power generating device including a hand lever. In detail, the power generating device is received in the receiving space 62 of the sole 60, and the hand lever resists against the upper wall of the receiving space 62. Thus, the sole 60 elastically deforms and restores from elastic deformation, forcing the hand lever to move back and forth alternately, so the power generating device generates induced current to power the vibration device 76.

In summary, if the users continually press or step on the sole 60, the power generating unit 71 generates induced current according to electromagnetic induction. The induced current is rectified, amplified and processed, and then is transmitted to the vibration device 76. The vibration device 76 starts to vibrate according to a predetermined vibration frequency to massage and stimulate the therapeutic points of the feet. Additionally, the electric energy from the power generating unit 71 can be stored within the power storage unit 75, as to power the vibration device 76 or charge an electronic device, which can add versatility and applicability of the therapeutic shoe 100.

In the present specification and claims the word "a" or "an" preceding an element does not exclude the presence of a plurality of such elements. Further, the word "comprising" does not exclude the presence of other elements or steps than those listed.

It is to be understood, however, that even though numerous characteristics and advantages of the exemplary disclosure have been set forth in the foregoing description, together with details of the structure and function of the exemplary disclosure, the disclosure is illustrative only, and changes may be made in detail, especially in matters of shape, size, and arrangement of parts within the principles of exemplary disclosure to the full extent indicated by the broad general meaning of the terms in which the appended claims are expressed.

What is claimed is:

1. A therapeutic shoe, comprising:
   a main body;
   a sole located at one side of the main body; the sole comprising a receiving space;
   a vibration layer located between the main body and the sole; and
   a power generating module, comprising:

a power generating unit located within the sole, the power generating unit for inducing and generating induced current, the power generating unit comprising a magnet and a coil aligned with the magnet, the magnet and the coil located in the receiving space, when the sole elastically deforming and restoring elastic deformation, the sole driving the magnet to reciprocate in the coil, the coil the cutting magnetic field lines of the magnet and generating induced current;

a rectifying circuit electrically connected to the power generating unit and is located within the sole; and a vibration device electrically connected to the rectifying circuit, wherein the rectifying circuit rectifies and processes the induced current from the power generating unit, the vibration device is located at the vibration layer and receives the processed induced current from the rectifying circuit to vibrate according to a predetermined vibration frequency in the vibration layer.

2. The therapeutic shoe as claimed in claim 1, wherein the sole is made of elastic material and is capable of elastically deforming and automatically restoring elastic deformation, and the sole further comprises a spring, the power generating unit and the rectifying circuit are received within the receiving space, and opposite ends of the spring are fixed at an upper wall and a bottom wall of the receiving space respectively.

3. The therapeutic shoe as claimed in claim 2, wherein the magnet is a permanent magnet and is located at the upper wall of the receiving space, the coil is an inductive coil and is located at the bottom wall of the receiving space.

4. The therapeutic shoe as claimed in claim 3, wherein the rectifying circuit is in electronic communication with the coil of the power generating unit and is capable of receiving, rectifying, amplifying, and converting the induced current from the coil into corresponding direct current.

5. The therapeutic shoe as claimed in claim 3, wherein the power generating module further comprises a first switch and a power storage unit, the first switch is a single pole double throw switch and comprises a common end, a first fixed contact and a second fixed contact, the common end of the first switch is in electronic communication with the rectifying circuit, and the first fixed contact and the second fixed contact of the first switch are electrically connected to the vibration device and the power storage unit respectively.

6. The therapeutic shoe as claimed in claim 5, wherein the power storage unit is a storage battery and is for storing electric energy from the rectifying circuit and providing the electric energy for the vibration device, when the common end of the first switch is switched on to electrically connect the second fixed contact of the first switch, the power storage unit electrically connects the rectifying circuit and receives and stores the electric energy from the rectifying circuit.

7. The therapeutic shoe as claimed in claim 6, wherein the vibration device is a vibrator or a vibrating motor, when the common end of the first switch is switched on to electrically connect the first fixed contact of the first switch, the rectifying circuit is electrically connected to and powers the vibration device, the vibration device is activated and vibrates according to the predetermined vibration frequency for continually stimulating and physically massaging therapeutic points of feet.

8. The therapeutic shoe as claimed in claim 6, wherein the power generating module further comprises an interface and an air treatment device, the interface is implemented to link one electronic device with another and is electrically connected to the power storage unit and the electronic device to power the electronic device, the air treatment device is located at the vibration layer and is electrically connected to the power storage unit.

9. The therapeutic shoe as claimed in claim 6, further comprising an insole located in the main body, wherein the insole is made from soft magnetic material and comprises a plurality of through holes, a plurality of massage projections and a plurality of metal sheets, the through holes are distributed on the insole for conducting ventilation and heat output, the massage projections are distributed and arranged on the surface of the insole corresponding to the therapeutic points of the feet for massaging and stimulating the therapeutic points through physical vibration, the metal sheets are distributed and located on the insole adjacent to the massage projections, corresponding to and aligned with the therapeutic points.

10. The therapeutic shoe as claimed in claim 9, wherein the power generating module further comprises a second switch, the second switch is a single pole double throw switch and comprises a first common end, a first fixed contact and a second fixed contact, the common end of the second switch electrically connects the power storage unit, and the first fixed contact and the second fixed contact of the second switch electrically connect the vibration device and the metal sheets respectively, when the common end of the second switch electrically connects the first fixed contact of the second switch, the power storage unit selectively connects and powers the vibration device, and the vibration device is activated and starts to vibrate based on the predetermined vibration frequency to stimulate and massage the therapeutic points, when the common end of the second switch connects the second fixed contact of the second switch, the power storage unit selectively connects the metal sheets to conduct the current from the power storage unit.

11. The therapeutic shoe as claimed in claim 3, wherein the sole further comprises an iron plate located on and adjacent to the magnet, the iron plate is for maintaining and enhancing the magnetism of the magnet.

12. A therapeutic shoe, comprising:
a sole comprising a receiving space;
a vibration layer located at one side of the sole; and
a power generating module, comprising:
a power generating unit for inducing and generating corresponding induced current by electromagnetic induction, the power generating unit comprising a magnet and a coil aligned with the magnet, the magnet and the coil located in the receiving space, when the sole elastically deforming and restoring elastic deformation, the sole driving the magnet to reciprocate in the coil, the coil cutting magnetic field lines of the magnet and generating induced current;
a rectifying circuit electrically connected to the power generating unit, the rectifying circuit for rectifying, amplifying and processing the induced current from the power generating unit;
a first switch electrically connected to the rectifying circuit;
a power storage unit electrically connected to the first switch, the power storage unit for storing and providing electric energy; and
a vibration device located at the vibration layer, wherein the power generating unit, the rectifying circuit, the first switch and the power storage unit are located within the sole, the first switch is selectively switched on to electrically connect the power storage unit or the vibration device, when the power storage unit is electrically connected to the rectifying circuit through the first switch, the power storage unit receives and stores the electric energy from the rectifying circuit; when the rectifying circuit is electrically connected to the vibration device through the first switch, the vibration device starts to vibrate according to a predetermined vibration frequency.

13. The therapeutic shoe as claimed in claim 12, wherein the sole is made of elastic material and is capable of elastically deforming and automatically restoring elastic deformation, and the sole further comprises a spring, the power generating unit, the rectifying circuit, the first switch and the power storage unit are received within the receiving space, and opposite ends of the spring are fixed at an upper wall and a bottom wall of the receiving space respectively.

14. The therapeutic shoe as claimed in claim 13, wherein the magnet is a permanent magnet and is located at the upper wall of the receiving space, the coil is an inductive coil and is located at the bottom wall of the receiving space.

15. The therapeutic shoe as claimed in claim 14, wherein the first switch is a single pole double throw switch and comprises a common end, a first fixed contact and a second fixed contact, the common end of the first switch is in electronic communication with the rectifying circuit, and the first fixed contact and the second fixed contact of the first switch are electrically connected to the vibration device and the power storage unit respectively.

16. The therapeutic shoe as claimed in claim 15, wherein the power storage unit is a storage battery, the vibration device is a vibrator or a vibrating motor, when the common end of the first switch is electrically connected to the second fixed contact of the first switch, the power storage unit electrically connects the rectifying circuit and receives and stores the electric energy from the rectifying circuit, when the common end of the first switch is electrically connected to the first fixed contact of the first switch, the rectifying circuit electrically connects and powers the vibration device, the vibration device is activated and vibrates according to the predetermined vibration frequency for continually stimulating and physically massaging therapeutic points of feet.

17. The therapeutic shoe as claimed in claim 14, wherein the sole further comprises an iron plate located on and adjacent to the magnet, the iron plate is for maintaining and enhancing the magnetism of the magnet.

18. The therapeutic shoe as claimed in claim 12, wherein the power generating module further comprises an interface and an air treatment device, the interface implemented to link one electronic device with another is electrically connected to the power storage unit and the electronic device to power the electronic device, the air treatment device is located at the vibration layer and is electrically connected to the power storage unit.

19. The therapeutic shoe as claimed in claim 12, further comprising an insole located in the main body, wherein the insole is made from soft magnetic material and comprises a plurality of through holes, a plurality of massage projections and a plurality of metal sheets, the through holes are distributed on the insole for conducting ventilation and heat output, the massage projections are distributed and arranged on the surface of the insole corresponding to the therapeutic points of the feet for massaging and stimulating the therapeutic points through physical vibration, the metal sheets are distributed and located on the insole adjacent to the massage projections, corresponding to and aligned with the therapeutic points.

20. The therapeutic shoe as claimed in claim 19, wherein the power generating module further comprises a second switch, the second switch is a single pole double throw switch and comprises a first common end, a first fixed contact and a second fixed contact, the common end of the second switch connects the power storage unit, and the first fixed contact and the second fixed contact of the second switch connect the vibration device and the metal sheets respectively, when the common end of the second switch connects the first fixed contact of the second switch, the power storage unit connects and powers the vibration device, the vibration device is activated and starts to vibrates according to the predetermined vibration frequency to stimulate and massage the therapeutic points, when the common end of the second switch connects the second fixed contact of the second switch, the power storage unit selectively and electrically connects the metal sheets to conduct the current from the power storage unit.

* * * * *